United States Patent
Clark

(10) Patent No.: US 11,925,508 B2
(45) Date of Patent: Mar. 12, 2024

(54) ULTRASOUND PROBE WITH THERMAL AND DROP IMPACT MANAGEMENT

(71) Applicant: KONINKLIJKE PHILIPS N.V., Eindhoven (NL)

(72) Inventor: Dennis Dean Clark, Lewistown, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1161 days.

(21) Appl. No.: 16/318,046

(22) PCT Filed: Jul. 28, 2017

(86) PCT No.: PCT/EP2017/069102
§ 371 (c)(1),
(2) Date: Jan. 15, 2019

(87) PCT Pub. No.: WO2018/019974
PCT Pub. Date: Feb. 1, 2018

(65) Prior Publication Data
US 2021/0275151 A1    Sep. 9, 2021

Related U.S. Application Data

(60) Provisional application No. 62/368,267, filed on Jul. 29, 2016.

(51) Int. Cl.
*A61B 8/00* (2006.01)
*B06B 1/06* (2006.01)

(52) U.S. Cl.
CPC ............ *A61B 8/546* (2013.01); *A61B 8/4494* (2013.01); *B06B 1/0622* (2013.01)

(58) Field of Classification Search
None
See application file for complete search history.

(56) References Cited

U.S. PATENT DOCUMENTS 5,014,708 A * 5/1991 Hayashi ............... A61B 8/5238
600/105
5,465,724 A   11/1995 Sliwa, Jr. et al.
5,482,047 A * 1/1996 Nordgren ................. A61B 8/06
439/74

(Continued)

FOREIGN PATENT DOCUMENTS

CN    101103929 A    1/2008
CN    101166472 A    4/2008
(Continued)

*Primary Examiner* — Christopher Koharski
*Assistant Examiner* — Farouk A Bruce

(57) ABSTRACT

Systems, methods, and apparatuses for conducting heat from an ultrasound transducer and reducing drop impact forces are disclosed. A thermal management system including a thermally conductive compliant component in an ultrasound probe is disclosed. The thermal management system may include thermally conductive compliant component coupled to a transducer assembly. A printed circuit assembly (PCA) may be coupled to the compliant component. The thermally compliant component may conduct heat from the transducer assembly to the PCA. The PCA may be further coupled to a cable that may conduct heat from the PCA and away from the ultrasound probe.

17 Claims, 11 Drawing Sheets

(56) References Cited

U.S. PATENT DOCUMENTS

| | | | |
|---|---|---|---|
| 6,106,474 A * | 8/2000 | Koger | B06B 1/0674 600/467 |
| 8,574,159 B2 | 11/2013 | Kondoh | |
| 2004/0002655 A1* | 1/2004 | Bolorforosh | B06B 1/06 600/459 |
| 2004/0015084 A1* | 1/2004 | Flesch | A61B 8/4483 600/466 |
| 2004/0073118 A1* | 4/2004 | Peszynski | A61B 8/12 600/459 |
| 2005/0154311 A1 | 7/2005 | Bruestle | |
| 2005/0236930 A1* | 10/2005 | Hasegawa | B06B 1/067 310/322 |
| 2007/0287920 A1* | 12/2007 | Sawada | B06B 1/067 600/463 |
| 2008/0009742 A1* | 1/2008 | Kondoh | B06B 1/0622 600/459 |
| 2008/0188755 A1 | 8/2008 | Hart | |
| 2008/0194960 A1 | 8/2008 | Randall | |
| 2008/0194963 A1 | 8/2008 | Randall | |
| 2011/0071396 A1* | 3/2011 | Sano | G01N 29/2406 600/443 |
| 2011/0077557 A1* | 3/2011 | Wing | A61B 8/546 601/2 |
| 2011/0230794 A1 | 9/2011 | van Groningen et al. | |
| 2012/0197113 A1 | 8/2012 | Courtney et al. | |
| 2013/0172751 A1* | 7/2013 | Heinrich | A61B 8/4466 600/447 |
| 2013/0205904 A1 | 8/2013 | Ueberschlag et al. | |
| 2013/0301395 A1* | 11/2013 | Hebrard | A61B 8/546 367/189 |
| 2014/0058270 A1 | 2/2014 | Davidsen et al. | |
| 2017/0164926 A1* | 6/2017 | Spicci | A61B 8/4444 |

FOREIGN PATENT DOCUMENTS

| | | |
|---|---|---|
| CN | 101911178 A | 12/2010 |
| JP | 2001104356 A | 4/2001 |
| JP | 2004329495 A | 11/2004 |
| WO | 2006114736 A2 | 11/2006 |
| WO | 2009083896 A2 | 7/2009 |

* cited by examiner

ULTRASOUND PROBE WITH THERMAL AND DROP IMPACT MANAGEMENT

This application is the U.S. National Phase application under 35 U.S.C. § 371 of International Application No. PCT/EP2017/069102, filed on Jul. 28, 2017, which claims the benefit of Provisional Application Ser. No. 62/368,267, filed Jul. 29, 2016. These applications are hereby incorporated by reference herein.

BACKGROUND

Ultrasound transducer arrays produce ultrasound waves for a variety of applications such as imaging, cleaning, and therapeutic treatment of tissue. Many ultrasound transducers convert electrical energy into ultrasound waves, and heat may be produced as a byproduct of the conversion. The heat may require dissipation to avoid damaging the transducer and/or a surface with which the ultrasound transducer is in contact. For example, a medical ultrasound transducer may heat the lens sufficiently to burn the skin of a patient if heat produced by the transducer is not dissipated adequately.

Ultrasound probes may have active and/or passive thermal management systems. Passive systems may include materials that conduct heat away from the transducer. For example, an ultrasound probe may include a backing material below the transducer that may dissipate heat away from the transducer surface. The backing material may be connected to a metal frame inside the housing of the ultrasound probe. The transducer, backing material, and frame are typically rigidly coupled. The lens may also be rigidly coupled to the housing. The rigid connections may promote thermal conductivity and alignment of the transducer and lens within the housing of the ultrasound probe. However, if the ultrasound probe is dropped onto the exposed lens, the rigid connections may result in high peak impact forces on fragile acoustic elements of the transducer. The high impact forces may increase the likelihood of damage to the transducer.

SUMMARY

According to an exemplary embodiment of the disclosure, an ultrasound probe may include a transducer assembly that may include a lens, a transducer stack coupled to the lens, and a backing subassembly coupled to the transducer stack opposite the lens. The ultrasound probe may further include a printed circuit assembly (PCA) spaced from and coupled to the transducer assembly, a housing enclosing the PCA and at least a portion of the transducer assembly, and a compliant component disposed between the transducer assembly and the PCA and coupling the transducer assembly to the PCA. The compliant component may be configured to bias the transducer assembly away from the PCA towards a portion of the housing. In some embodiments, the compliant component may comprise a spring having a first end connected to a distal portion of the PCA and a second end connected to a proximal portion of the backing subassembly.

According to an exemplary embodiment of the disclosure, a thermal management system may include a backing subassembly of a transducer assembly, a cladding on an exterior surface of a printed circuit assembly (PCA), which may be spaced from and coupled to the backing subassembly, and a compliant component disposed between the backing subassembly and the cladding and coupling the backing subassembly to the cladding. The compliant component may be configured to enable a distance between the cladding and the backing subassembly to vary.

DETAILED DESCRIPTION

Figure 1:
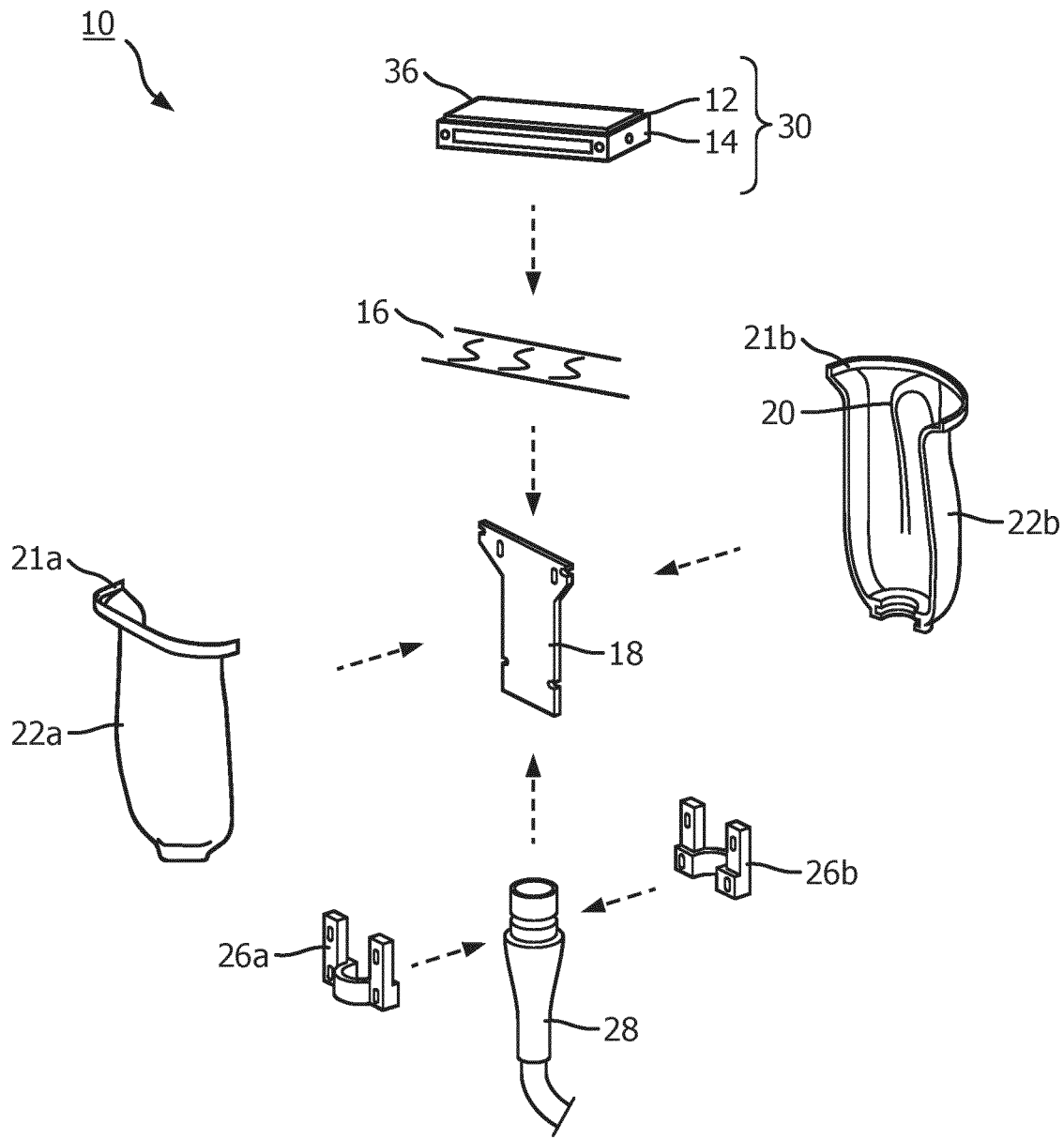
FIG. 1 is a schematic illustration of an exploded view of an ultrasound probe according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

An ultrasound probe may be used for imaging, medical therapy, or other applications. The ultrasound probe includes an ultrasound transducer to produce and receive ultrasound signals (e.g., waves, pulses, sequences). The transducer may generate heat as it produces and/or receives ultrasound signals. If the temperature of the transducer increases above a threshold temperature, the transducer and/or an object in contact with the transducer may be damaged.

To manage the increase in temperature of the transducer, the probe may include components to actively and/or passively dissipate the heat generated by the transducer. The components may include thermally conductive materials in thermal contact with the transducer and may conduct and/or dissipate heat from the transducer through one or more thermal paths. The components may be coupled to and/or in thermal contact with one another in the probe. The components may dissipate the heat over a wide area. The components for conducting heat from the transducer may be referred to generally as a thermal management system.

One or more components of the thermal management system may be compliant as well as thermally conductive. That is, the component may deform, compress, and/or move when a force is applied. In some embodiments, the compliant component may be coupled between two or more components of the thermal management system. In some embodiments, the compliant component may be coupled between a thermal management component and an ultrasound probe component, which may or may not be part of the thermal management system. In some embodiments, the compliant component may be coupled between two ultrasound probe components, which may or may not be part of the thermal management system. The compliant component may allow two or more components to move relative to one another in one or more dimensions. In some embodiments, the compliant component may maintain a space or distance between two or more components unless a force is applied to the compliant component and/or one of the other components or both.

The compliant component of the thermal management system may allow the ultrasound probe to resist damage from an impact force. For example, if the ultrasound probe is dropped, the compliant component may absorb at least some of the impact force by deforming, compressing, and/or moving. The compliant component may elastically deform and/or compress. In other words, the compliant component may return to its original position and/or state after the force is removed. This may reduce and/or prevent damage to one or more components of the ultrasound probe. For example, the compliant component may be coupled between a backing subassembly of a transducer assembly and a printed circuit assembly (PCA) in an ultrasound probe housing. The compliant component may allow a space between the transducer assembly and the PCA to vary (e.g., decrease) when a force is applied to the transducer assembly. When the ultrasound probe is dropped, it may land on a lens at a distal end of the transducer assembly. At least a portion of the force on the lens may be transferred to the compliant component, and the compliant component may deform. The space between the PCA and the transducer assembly may decrease, at least temporarily, when the force is applied to the lens. The compliant component may reduce the impact force on the lens of the transducer assembly. This may reduce the damage to the lens, other components of the transducer assembly, and/or other ultrasound probe components.

FIG. 1 is a schematic illustration of an exploded view of an ultrasound probe 10 according to an embodiment of the disclosure. As used herein, distal refers to an end of the ultrasound probe that is typically closest to and/or in contact with a subject or object to be imaged during use. Proximal refers to an end of the ultrasound probe that is typically farther from the subject or object to be imaged and/or closer to an ultrasound imaging system (not shown) during use.

The ultrasound probe 10 may include a housing 22 which may form the handle portion of the probe that is held by a sonographer during use. The housing 22 is shown as having two portions 22a-b, which may be configured to mate to form the housing 22. However, the housing 22 may be a unitary body and/or be composed of more than two portions configured to mate in some embodiments. When the two portions 22a-b of the housing 22 are joined, the housing 22 may define an opening (not numbered) at a distal end of the probe 10 that may expose at least a portion of a lens 36 of a transducer assembly 30. The transducer assembly 30 may include the lens 36 at the distal end, a transducer stack 12 on the proximal side of the lens 36, and a backing subassembly 14 on the proximal side of the transducer stack 12. The transducer stack 12 may be between the lens 36 and the backing subassembly 14. The transducer stack 12 may include a matrix array transducer or another transducer type. The transducer assembly 30 may include a flexible circuit and/or other electrical components (not shown). In some embodiments, the flexible circuit may be included in the transducer stack 12. The flexible circuit and/or electrical components may couple the transducer or other components of the transducer stack 12 to other electrical components of the ultrasound probe 10. The backing subassembly 14 may include components of a thermal management system. The backing subassembly 14 may attenuate acoustic reverberations from the back of the transducer stack 12 and/or may conduct heat developed in the transducer stack 12 away from the distal end of the probe 10. The backing subassembly 14 may include a graphite block in some embodiments. In some embodiments, the backing subassembly 14 may include a thermally conductive block and/or backing. The block and/or backing may replace or be in addition to the graphite block. In some embodiments, the block and/or backing may comprise aluminum. Although the transducer assembly 30 is shown as having a substantially rectangular shape, the transducer assembly 30 may have other shapes. Example suitable shapes include, but are not limited to, a dome, an arc, and a half-cylinder. The shape of the transducer assembly 30 may be determined, at least in part, by the ultrasound imaging application (e.g., thoracic, cardiac, esophageal).

The probe 10 may include a PCA 18 may include electrical circuits and/or other electrical components for operation of the ultrasound probe 10. In some embodiments, the PCA 18 may include one or more thermal management system components. In some embodiments, the PCA 18 may include a cladding (not shown in FIG. 1) that may conduct heat from the compliant component 16 to the proximal end of the probe 10. In some embodiments, the PCA 18 may include a thermally conductive material, which is thermally-conductively coupled to the transducer assembly 30 to conduct heat from the transducer assembly 30.

In some examples, the PCA 18 may be thermally-conductively and mechanically coupled to the transducer assembly in part by a compliant component 16 disposed between the PCA 18 and the transducer assembly 30. The compliant component 16 may be coupled to the proximal end of the transducer assembly 30 (e.g., to the proximal portion of the backing subassembly 14) and to the distal end of a printed circuit assembly (PCA) 18. The compliant component 16 may be thermally conductive and conduct heat away from the distal end of the probe 10. The compliant component 16 may be a component of the thermal management system. The compliant component 16 may be resiliently deformable such that a dimension (e.g., a length) of the compliant component 16 decreases when force is applied along that dimension and the dimension (e.g. length) returns to its nominal in the absence of the application of force. In some embodiments, the compliant component 16 includes a spring, for example a compression spring. The compliant component 16 may be implemented using copper (Cu), a copper beryllium alloy (CuBe), and/or a combination of thermally conductive materials. In some embodiments, the compliant component 16 may comprise a ½ hard or ¼ hard copper material. In some embodiments, the compliant component 16 includes a combination of thermally conductive and nonconductive materials.

The PCA 18 may be coupled to a flexible circuit (not shown) or other electrical components of the transducer assembly 30. The PCA 18 may be coupled to the housing 22. In some embodiments, the PCA 18 may be press-fit into the housing 22. In some embodiments, the PCA 18 may be heat staked to the housing 22. In some embodiments, the PCA 18 may be coupled to a post (not shown in FIG. 1) protruding from an interior surface 21 of the housing 22.

At the proximal end of the probe 10 and extending therefrom may be a cable 28. In some embodiments, the cable 28 may be a coaxial cable. In some embodiments, the cable 28 may be clamped to a proximal end of the PCA 18 by a clamp 26a-b. Other attachment methods may also be used. The cable 28 may couple the probe 10 to an ultrasound imaging system (not shown). In some embodiments, the cable 28 may include a metal braid (not shown), which may be in thermal contact with the PCA 18 and/or backing subassembly 14. The metal braid may conduct heat from the PCA 18 and/or backing subassembly 14 along the cable 28.

The PCA 18, compliant component 16, and/or other internal components of the probe 10 may be enclosed in the housing 22. The housing 22 may include two separate portions 22a-b that may be configured to fit together with each other to form an impervious housing to protect the ultrasound components from electromagnetic field interference, liquids, and/or debris. The housing 22 may comprise plastic, metal, rubber, and/or a combination of materials. In some embodiments, the housing 22 may be configured to enclose the transducer stack 12 and backing subassembly 14 of the transducer assembly 30 while leaving at least a portion of the lens 36 exposed.

In some embodiments, the housing 22 may include a handle heat spreader 20 on the interior surface 21a-b of each portion of the housing 22a-b (Only one handle heat spreader 20 is visible in FIG. 1). In some embodiments, the handle heat spreader 20 may be included only on one of the interior surfaces 21a-b. The handle heat spreader 20 may be a component of a probe thermal management system. The handle heat spreader 20 may include a copper layer. Other metals and/or thermally conducting materials may be used. The handle heat spreader 20 may be coupled to the housing 22 by an adhesive or another attachment method may be used. The handle heat spreader 20 may conform to the interior surface 21a-b of the housing 22a-b. The handle heat spreader 20 may be coupled to one or more other components of the thermal management system. For example, the handle heat spreader 20 may be thermally coupled to one or more sides of the backing subassembly 14, the cable 28, and/or PCA 18.

Figure 2:
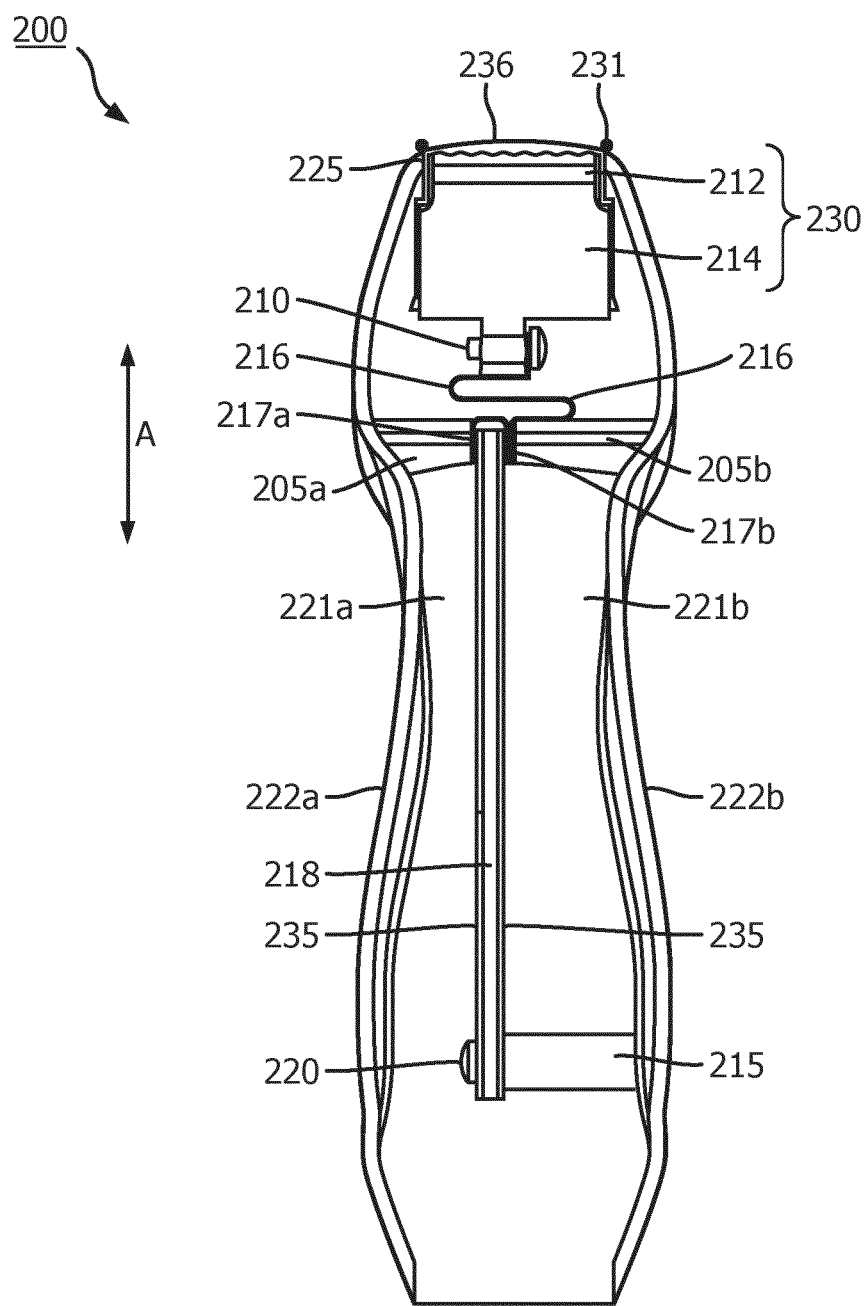
FIG. 2 is a schematic illustration of a side cross-sectional view of an ultrasound probe according to another embodiment of the disclosure.

FIG. 2 is a schematic illustration of a side cross-sectional view of an ultrasound probe 200 according to an embodiment of the disclosure. Components that correspond to like or similar components of ultrasound probe 10 shown in FIG. 1 have reference numbers with corresponding lower digits when possible. In some embodiments, components of probe 200 that correspond to same or similar components of probe 10 may have the same or similar properties to the corresponding components of probe 10. As shown in FIG. 2, a lens 236 of a transducer assembly 230 is at least partially exposed to the exterior of the ultrasound probe housing 222 through an opening 225 in the ultrasound probe housing 222 at a distal end of the ultrasound probe 200. The lens 236 may come into contact with a patient or an object to be imaged by the ultrasound probe 200. In some embodiments, a sealant 231, which may comprise an elastic material, may be provided at the interface between the distal end of the transducer assembly 230 and the opening 225. For example, an elastic sealant may be disposed along a periphery of the lens 236, e.g., along a portion of the lens 236 which abuts the portion of the housing that defines the opening 225. In the illustrated embodiment, the size and/or shape of the sealant 231 may be exaggerated for illustration purposes. In some embodiments, the sealant 231 may be substantially flush with the exterior surfaces of the housing 222 and lens 236. The sealant 231 may allow at least some relative movement between the housing 222 and the lens 236, for example in a dimension indicated by arrow A. The sealant 231 may be configured to prevent liquid and/or debris from entering the interior of the ultrasound probe 200. In some embodiments, the elastic material 230 may be a low modulus adhesive.

The transducer assembly 230 may be coupled to a thermally conductive compliant component 216 at a proximal end of a backing subassembly 214 of the transducer assembly 230. The compliant component 216 may be defined by a shaped strip of metal which is configured to resiliently deform to change a distance between the ends of the metal strip. For example, the compliant component 216 may comprise two or more substantially parallel portions of a metal strip spaced apart and joined by one or more substantially perpendicular portions of the metal strip. In some examples, the compliant component may be C-shaped, S-shaped, Z-shaped, helically shaped, or have a different shape that enables deformation of the compliant component along a compression direction. In some embodiments, the compliant component may include a plurality of springs or may be a resiliently deformable block of thermally conductive material.

In the embodiment shown in FIG. 2, the compliant component 216 is a metal S-shaped spring. In some embodiments, the S-shaped spring is formed from a strip of metal. As discussed previously, the compliant component 216 may be copper, a copper alloy, and/or other thermally conductive material. The compliant component 216 may be clamped, welded, screwed, or riveted to the backing subassembly 214. In some embodiments, the compliant component 216 may be coupled to the backing subassembly 214 by a combination of methods. In the embodiment shown in FIG. 2, the compliant component 216 is coupled to the backing subassembly 214 by a screw 210. More than one screw may be used. The screw 210 may pass through a hole (not shown) in the backing subassembly 214. In some embodiments, the screw 210 may be coated. For example, the screw 210 may have a nylon-based coating. The coating may improve thermal conductivity, reduce vibration, and/or reduce loosening of the screw 210. In some embodiments, a thermal laminate may be applied between the backing subassembly 214 and the compliant component 216. The thermal laminate may improve thermal conductivity between the backing subassembly 214 and the compliant component 216.

The compliant component 216 may be coupled to a distal end of a printed circuit assembly (PCA) 218. The PCA 218 may include a cladding 235 on one or more outer surfaces of the PCA 218. The cladding 235 may be thermally conductive. The cladding 235 may be implemented using copper, copper alloy, and/or other thermally conductive material. In some embodiments, the compliant component 216 is thermally coupled to the cladding 235. The compliant component 216 may be welded, soldered, clamped and/or screwed to the cladding 235. Other coupling methods may be used. In the embodiment shown in FIG. 2, the compliant component 216 includes a pair of flanges 217a-b that are coupled to the cladding 235. Each flange in the pair may be provided on opposite side of the PCA 218 and may be attached thereto using conventional techniques (e.g., bonding, welding, mechanically fastening, etc.) In some embodiments, the PCA 218 may alternatively or additionally be frictionally retained between the flanges 217a-b. In the illustrated embodiment, the proximal portion of the spring is shaped to define a pair of two generally parallel downward extending portions which function as the flanges 217a-b. In some embodiments, a thermal laminate may be applied between the compliant component 216 and the cladding 235.

The PCA 218 in this embodiment is coupled to the housing 222 at a proximal end of the PCA 218, however in other embodiments, the PCA 218 may be coupled to the housing 222 anywhere along the length of the PCA 218. Multiple coupling methods or combinations of methods may be used. In the embodiment shown in FIG. 2, the PCA 218 is coupled to the housing 222 by a post 215 protruding from an interior surface 221b of the housing 222b. The PCA 218 is coupled to the post 215 by a screw 220 that passes through the PCA 218 and engages with the post 215. In some embodiments, the PCA 218 may be held in a position within the housing 222 by alternative or additional methods. For example, the PCA 218 may be frictionally retained in a transverse seat defined by the post. In other examples, the PCA 218 may be held in place between opposing posts extending from opposite interior surfaces 221a and 221b of the housing 222. In the embodiment shown in FIG. 2, the PCA 218 is additionally and optionally constrained between posts 205a-b protruding from interior surfaces 221a-b of housing 222a-b at the distal end of the PCA 218. In the illustrated embodiment, the posts 205a-b are arranged to reduce or eliminate movement of the distal end of the PCA 218 relative to the housing 222. In some embodiments, post 205a and post 205b are configured to engage each other through a hole (not shown) in the PCA 218. For example, posts 205a-b may be alternate bosses and crush ribs. In another example, post 205a may be sized to be press fit within a hole in post 205b. In some embodiments, posts 205a-b are configured to press against exterior surfaces of the PCA 218 to constrain the PCA 218. Other engagement methods may be used. Any suitable attachment mechanism may be used to rigidly couple the PCA 218, or at least a portion thereof, to the housing 222. The PCA 218 may be coupled at the proximal end to a cable (not shown in FIG. 2) in a similar manner as described with reference to FIG. 1.

Figure 3:
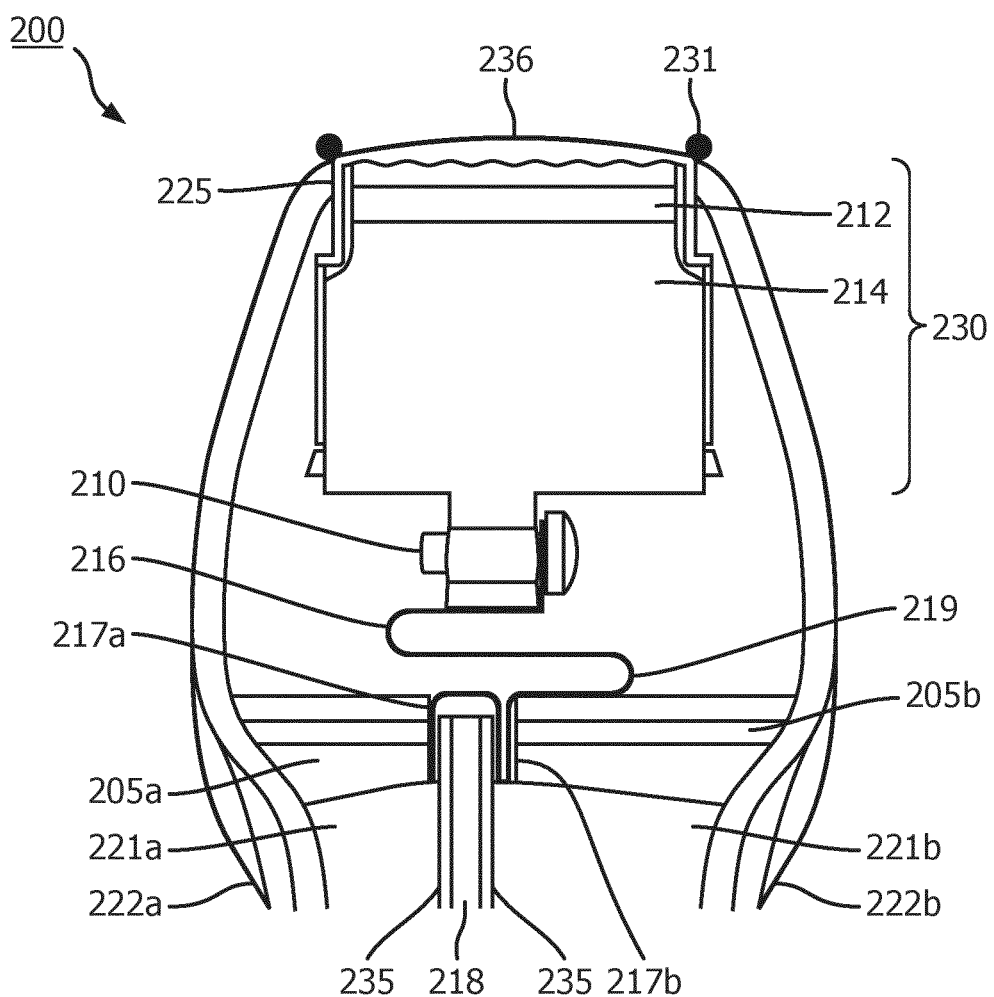
FIG. 3 is a schematic illustration of a partial side cross-sectional view of the ultrasound probe shown in FIG. 2, showing an enlarged view of the distal end of the ultrasound probe shown in FIG. 2.

FIG. 3 is an enlarged side cross-sectional view of a portion of the ultrasound probe, specifically of the distal end of the ultrasound probe 200, shown in FIG. 2. The compliant component 216 may allow for movement of the transducer assembly 230 relative to the PCA 218, for example along a dimension indicated by the arrow A. For example, the compliant component 216 may enable a distance between the transducer assembly 230 and the PCA 218 to increase and/or decrease. When assembled into the transducer probe, the range of movement of the transducer assembly 230 may be constrained by engagement between the transducer assembly 230 and the housing 222 at or near the distal end of the probe 200. In other words, when assembled, the transducer assembly 230 is biased away from the PCA 218 by the compliant component 216. The compliant component 216 biases the transducer assembly 230 towards the distal end of the housing 222 to force the lens assembly 236 into contact with the housing 222. The distal end of the transducer assembly 230 may be frictionally retained by the housing 222 (e.g., without bonding or fastening the transducer assembly 230 to the housing 222). In other embodiments, the transducer assembly 230 may be resiliently bonded to the housing 222 (e.g., via an adhesive compliant sealant 231) along opening 225.

The housing 222 and transducer assembly 230 may be shaped to engage one another and/or include features configured to engage, as will be described in more detail with reference to FIGS. 5 and 6. Movement of the transducer assembly 230 along the longitudinal direction (e.g., as indicated by arrow A) may additionally and optionally be constrained by engagement between the posts 205a-b and the compliant component 216. For example, the compliant component 216 may include a stop feature 219, which is arranged to operatively engage one or both of the posts 205a-b to limit the downward movement of the transducer assembly 230. The stop feature 219 may be provided by the shape of the metal strip. For example, a surface of the shaped metal strip may be arranged to press against one or both of the posts 205a-b to limit the downward movement of transducer assembly 230. In some embodiments, the compliant component 216, which is disposed between the PCA 218 and the transducer assembly 230, may be at least partially compressed when the ultrasound probe 200 is assembled. The compression may be applied to the compliant component 216 by the housing 222 by virtue of rigidly coupling the PCA 218 to the housing 222 and pressing the transducer assembly 230 against the housing 222. The compression of the compliant component 216 may cause the compliant component 216 to bias or urge the transducer assembly 230 against the housing 222 at the distal end of the probe 200. The biasing force applied by the compliant component 216 to the transducer assembly 230 may maintain alignment between the housing 222 and the transducer assembly 230.

A compliant coupling of the transducer assembly 230 to the housing 222 as described herein may reduce damage to the transducer assembly 230. For example, if a force is experienced by the transducer assembly 230 such as due to acceleration resulting for example from dropping the probe 200, the compliant component 216 may allow the transducer assembly 230 to move slightly relative to the housing such that any loads applied to the housing 222 are not transferred to the transducer assembly 230 as may be the case if the housing 222 and transducer assembly 230 were rigidly connected. In some embodiments, the posts 205a-b may prevent movement of the transducer assembly 230 beyond the posts 205a-b. This may prevent excessive movement of the transducer assembly 230 relative to the housing and internal components (e.g., the PCA 218), which reduces the risk of damage to the transducer assembly 230 and internal components (e.g., the PCA 218 or other internal components of the probe 200). In some embodiments, the sealant 231 may deform when a force is applied to the lens 236. The transducer assembly 230 may move towards the proximal end of the ultrasound probe 200 within the interior of the housing 222 when a force is applied to the lens 236. In some embodiments, the sealant 231 may maintain a seal between the housing 222 and the lens 236 along a periphery of the opening 225 even when a force is applied to the lens 236.

Figure 4:
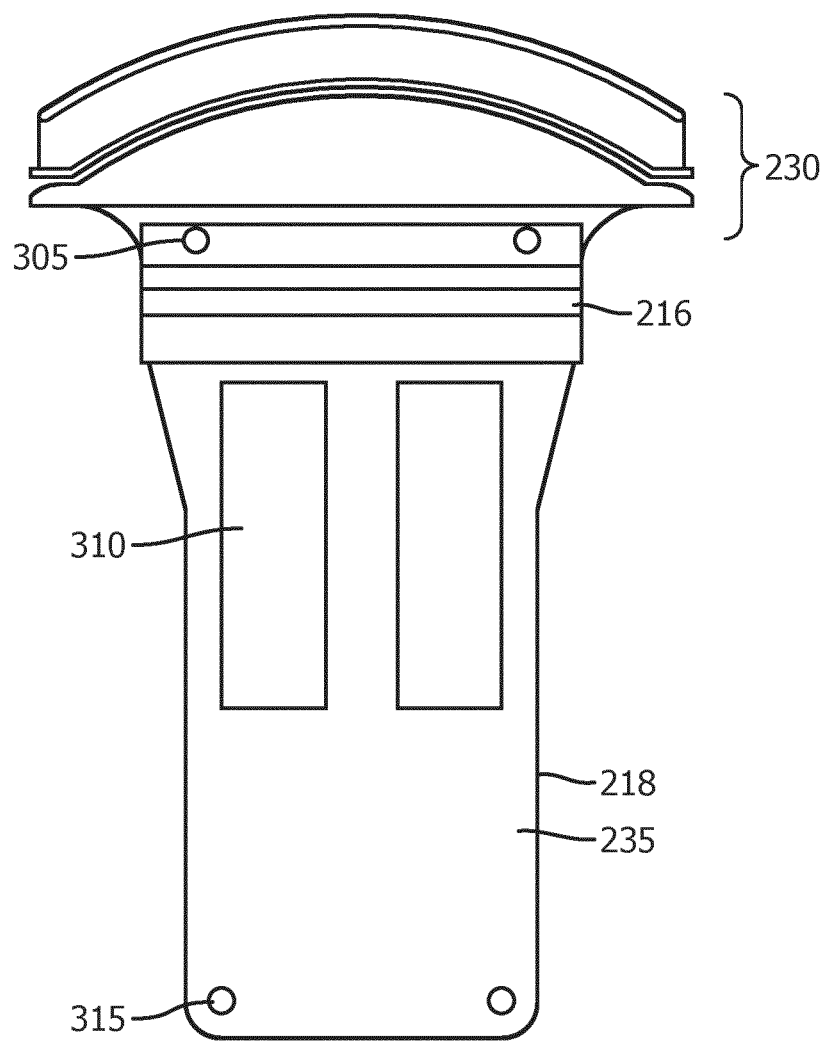
FIG. 4 is a schematic illustration of components of an ultrasound probe shown in FIG. 2.

FIG. 4 is a front view of the transducer assembly 230, compliant component 216, and PCA 218 of the ultrasound probe 200 shown in FIGS. 2-3. In some embodiments, as shown in FIG. 4, the compliant component 216 may include holes 305 for mechanical fasteners (e.g., screws 210, not shown in FIG. 4) for coupling the compliant component 216 to the transducer assembly 230. Similarly, in some embodiments, as shown in FIG. 4, holes 315 may pass through the PCA 218, including the cladding 235 of the PCA 218. The holes 315 may engage screws 220 (Not shown in FIG. 4) for coupling the PCA 218 to the housing 222 (not shown) of the probe 200. Any number of holes and corresponding fasteners may be used to couple the transducer assembly 230 to the compliant component 216, and the PCA 218 to the housing. The cladding 235 may be patterned to define windows 310. The windows 310 may provide access to electrical connections of the PCA 218. The windows 310 may allow a flexible circuit (not shown) of the transducer assembly 230 to be coupled to the circuitry on the PCA 218. Although two windows 310 are shown, more or fewer windows may be used in some embodiments.

In some embodiments, heat from the transducer assembly 230 may be conducted through the compliant component 216 to the distal end of the PCA 218. The heat may be conducted from the distal end to the proximal end of the PCA 218. In some embodiments, the heat may be conducted by the cladding 235 of the PCA 218. In some embodiments, at least a portion of the transducer assembly 230 (e.g., backing subassembly 214), the compliant component 216, at least a portion of the PCA 218 (e.g., cladding 235), and/or at least a portion of the cable (e.g., metal braid) may be components of a thermal management system of the ultrasound probe 200.

Figure 5:
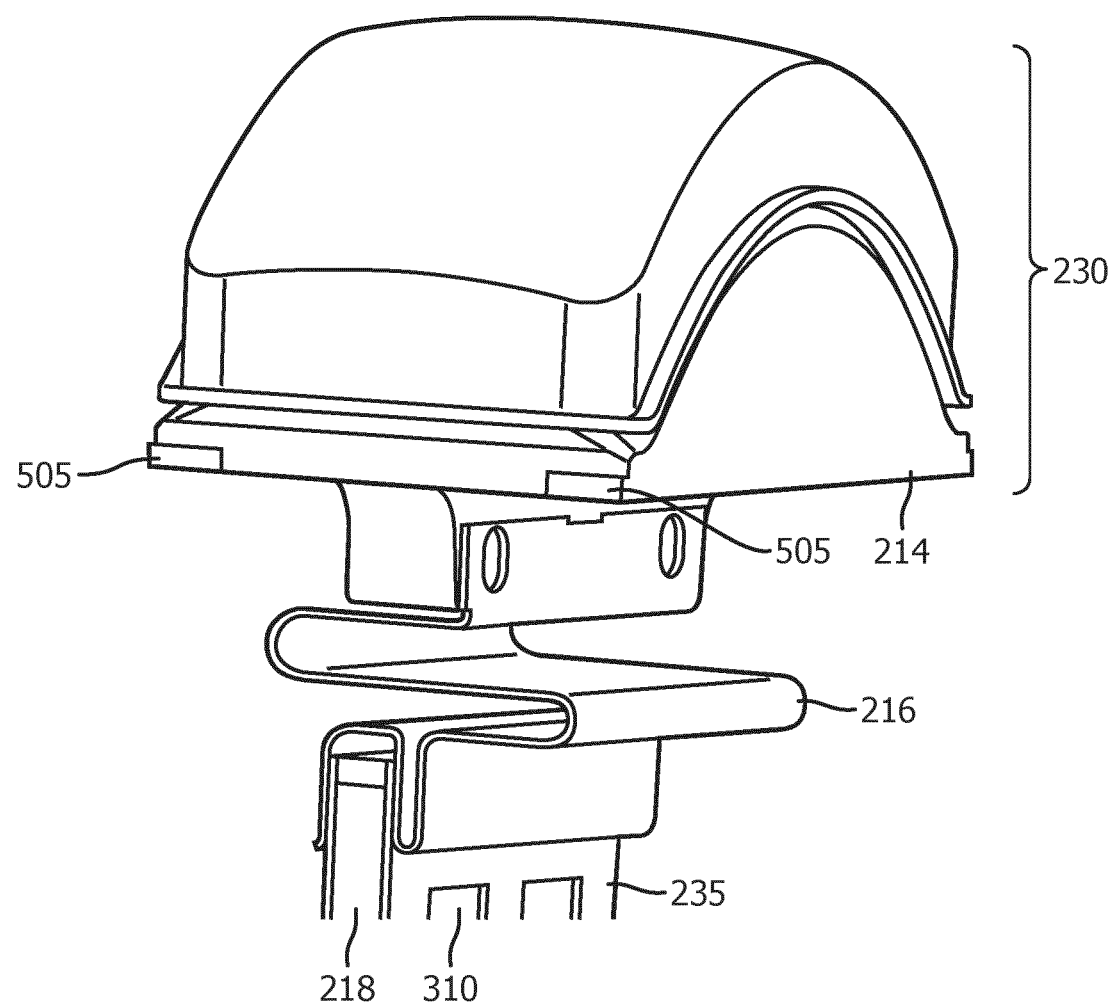
FIG. 5 is another schematic illustration of some of the components shown in FIG. 4.

FIG. 5 is an isometric view of the transducer assembly 230, compliant component 216, and PCA 218 of the ultrasound probe 200 shown in FIG. 4. In some embodiments, the transducer assembly 230 may be shaped to mate with the housing 222 of the ultrasound probe 200. For example, the backing subassembly 214 may be shaped to engage with an interior surface 221 of the housing 222. In some embodiments, the transducer assembly 230 may include features configured to engage with features of the housing 222. For example, in the embodiment shown in FIG. 5, the backing subassembly 214 includes tabs 505. The tabs 505 may be configured to engage ribs (not shown) on the interior surface 221 of the housing 222. When the compliant component 216 is at least partially compressed, the compliant component 216 may apply a biasing force on the transducer assembly 230 (e.g., a force away from the PCA and towards the housing), which may bias the tabs 505 of the backing subassembly 214 against the ribs of the housing 222. Features such as the tabs 505 and ribs may maintain alignment of the transducer assembly 230 with the housing 222. In some embodiments, the transducer assembly 230 may additionally or alternatively include ribs or a rim that extends from a periphery of the backing subassembly 214 or from a periphery of the lens. The ribs or rim may be configured to engage with ribs or other features of the housing 222. In some embodiments, the tabs 505 and/or other features of the backing subassembly 214 (e.g., ribs, rim), may be included on the lens 236 in addition to or instead of on the backing subassembly 214.

Figure 6:
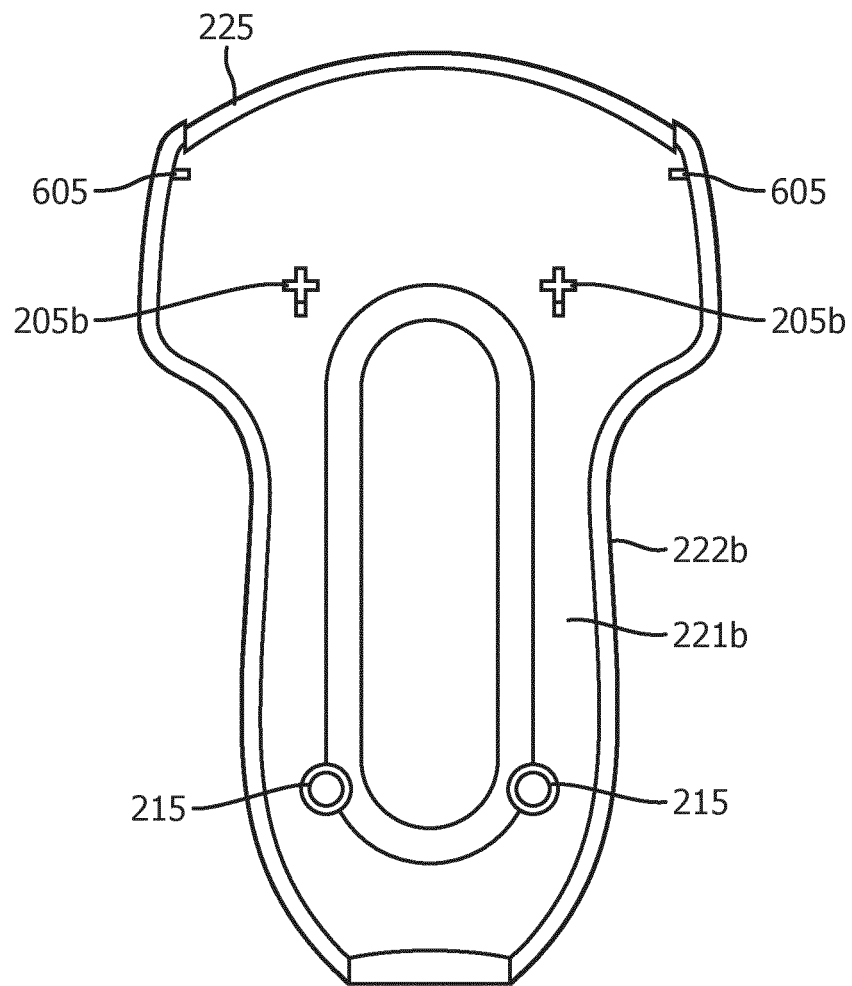
FIG. 6 is a schematic illustration of the housing of the ultrasound probe shown in FIG. 2.

FIG. 6 is a front view of housing 222b of probe 200 shown in FIGS. 2-3. Housing 222b may include ribs 605 on an interior surface 221b at the distal end of the ultrasound probe 200. The ribs 605 may be near the opening 225 in some embodiments. The ribs 605 may be configured to engage tabs 505 of the backing subassembly 214 shown in FIG. 5. In some embodiments, ribs 605 may be configured to engage ribs or a rim of the backing subassembly 214. In some embodiments, housing 222b may be a mirror image of housing 222a. In some embodiments, housing 222a or 222b may include additional or fewer features compared to one another. For example, in some embodiments, housing 222a (not shown in FIG. 6) may not include posts 215.

Figure 7:
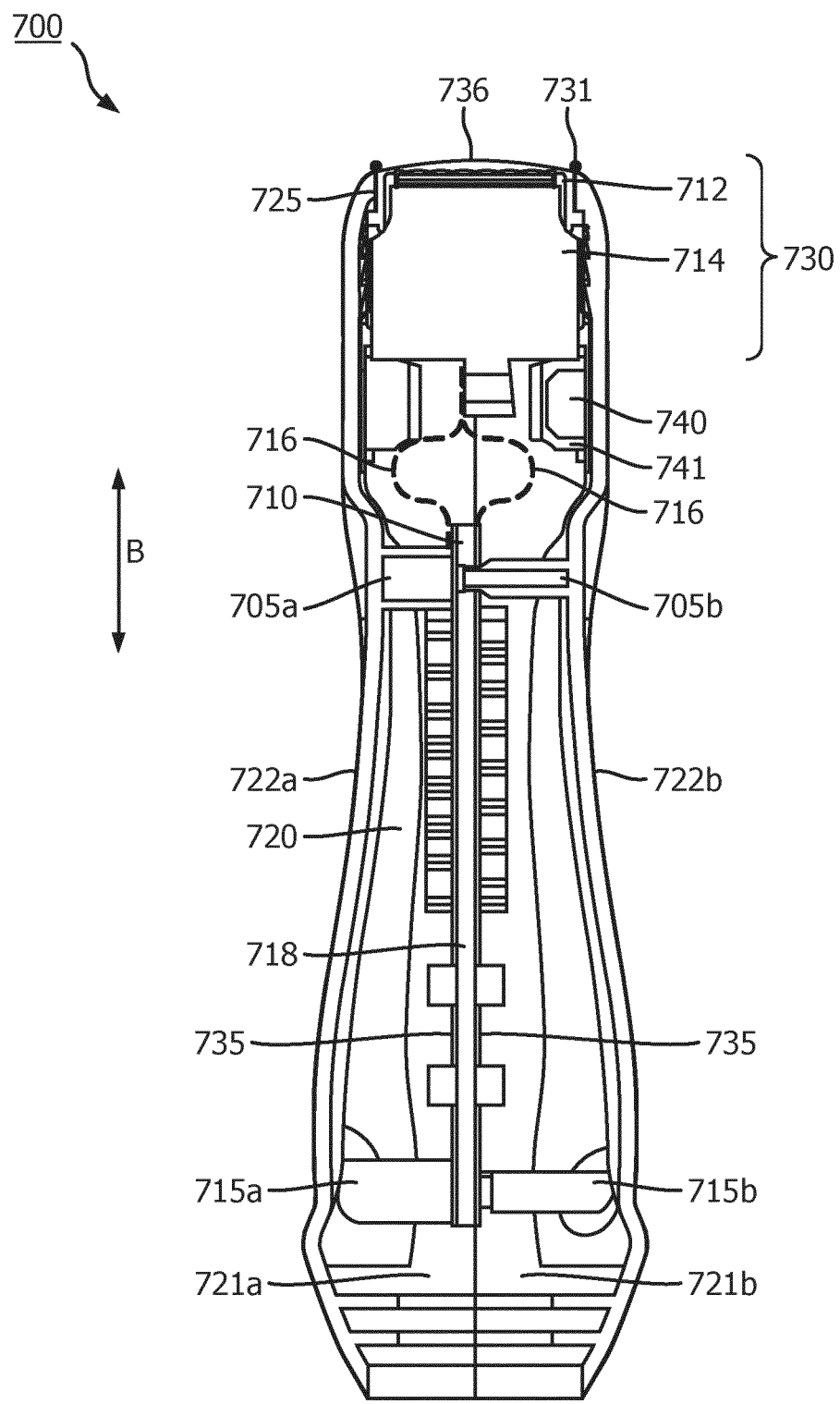
FIG. 7 is a schematic illustration of a side cross-sectional view of an ultrasound probe according to a further embodiment of the disclosure.

FIG. 7 is a schematic illustration of a side cross-sectional view of an ultrasound probe 700 according to an embodiment of the disclosure. Components that correspond to like or similar components of ultrasound probe 10 shown in FIG. 1 have reference numbers with corresponding lower digits when possible. In some embodiments, components of probe 700 that correspond to same or similar components of probe 10 may have the same or similar properties to the corresponding components of probe 10. As shown in FIG. 7, a lens 736 of a transducer assembly 730 is at least partially exposed through an opening 725 in an ultrasound probe housing 722 at a distal end of the ultrasound probe 700. The lens 736 may come into contact with a patient or an object to be imaged by the ultrasound probe 700. In some embodiments, a sealant 731, which may comprise an elastic material, may couple the lens 736 to the housing 722. For example, an elastic sealant may be disposed along a periphery of the lens 736, e.g., along a portion of the lens 736 which abuts the portion of the housing that defines the opening 725. In the illustrated embodiment, the size and/or shape of the sealant 731 may be exaggerated for illustration purposes. In some embodiments, the sealant 731 may be substantially flush with the exterior surfaces of the housing 722 and lens 736. The sealant 731 may allow at least some relative movement between the housing 722 and the lens 736, for example in a dimension indicated by arrow B. The sealant 731 may prevent liquid and/or debris from entering the interior of the ultrasound probe 700. In some embodiments, the sealant 731 may be a low modulus adhesive.

The transducer assembly 730 may be coupled to a thermally conductive compliant component 716 at a proximal end of a backing subassembly 714. In the embodiment shown in FIG. 7, the compliant component 716 comprises two metal C-shaped springs. As shown in FIG. 7, the C-shaped springs may comprise strips of metal. The compliant component 716 (e.g., C-shaped springs in this embodiment) may couple the transducer assembly 730 to the PCA 718 and may bias the transducer assembly 730 away from the PCA 718 and towards the housing 722. For example, each of the C-shaped springs may be connected, at one end, to a proximal portion of the transducer assembly 230 and at an opposite end, to a distal end of the PCA 718. In the illustrated embodiment, each of the springs is connected to opposite sides of the PCA 718 to provide two thermally conductive paths to components of the thermal management system on the PCA 718. As discussed previously, the compliant component 716 may be copper, a copper alloy, and/or other thermally conductive material. The compliant component 716 may be clamped, welded, screwed, or riveted to the backing subassembly 714. In some embodiments, the compliant component 716 may be coupled to the backing subassembly 714 by a combination of methods. In some embodiments, a thermal laminate may be applied between the backing subassembly 714 and the compliant component 716. The thermal laminate may improve thermal conductivity between the backing subassembly 714 and the compliant component 716.

As described, the compliant component 716 may be coupled to a distal end of a printed circuit assembly (PCA)

718. The PCA 718 may include a cladding 735 on one or more outer surfaces. The cladding 735 may be thermally conductive. The cladding 735 may be implemented using copper, copper alloy, and/or other thermally conductive material. In some embodiments, the compliant component 716 is thermally coupled to the cladding 735. The compliant component 716 may be welded, clamped and/or screwed to the cladding 735. In some embodiments, a thermal laminate may be applied between the compliant component 16 and the cladding 735.

As shown in the embodiment in FIG. 7, the PCA 718 may be coupled to the housing 722 at a proximal end of the PCA 718, however in other embodiments, the PCA 718 may be coupled to the housing 722 anywhere along the length of the PCA 718. Multiple coupling methods or combinations of methods may be used. In the embodiment shown in FIG. 7, the PCA 718 is coupled to the housing 722 by posts 715*a-b* protruding from interior surfaces 721*a-b* of the housing 722*a-b*. Posts 715*a* and/or 715*b* may be configured to pass through a hole (not shown) in the PCA 718 and engage with the corresponding post through the hole. In some embodiments, the PCA 718 may be held in a position within the housing 722 by alternative or additional methods such as those described with reference to FIGS. 1 and 2, for example. In the embodiment shown in FIG. 7, the PCA 718 is constrained between posts 705*a-b* on interior surfaces 721*a-b* of housing 722*a-b* at the distal end of the PCA 718. In some embodiments, post 705*a* and post 705*b* are configured to engage each other through a hole 710 in the PCA 718. For example, posts 705*a-b* may be alternate bosses and crush ribs. In another example, post 705*a* may be sized to be press fit within a hole in post 705*b*. Other engagement methods may be used. In some embodiments, posts 705*a-b* and posts 715*a-b* may have the same or similar structures. The PCA 718 may be further coupled at the proximal end to a coaxial cable (not shown in FIG. 7) in a similar manner as described with reference to FIG. 1.

The compliant component 716 may allow for movement of the transducer assembly 730 relative to the PCA 718, for example along a dimension indicated by the arrow B. That is, the compliant component 716 may be configured to allow a distance or spacing between the transducer assembly 730 and the PCA 718 to vary. The range of movement of the transducer assembly 730 may be limited by engagement between the transducer assembly 730 and the housing 722 at or near the distal end of the probe 700 and/or by stop features of the compliant component 716. The housing 722 and lens 736 and/or backing subassembly 714 may be shaped to engage one another and/or include features configured to engage, as will be described in more detail with reference to FIGS. 8 and 10. In some embodiments, the range of motion may be constrained by engagement between the proximal end of the backing subassembly 714 and/or distal end of the compliant component 716 with boss 740 protruding from the interior surface 721 of the housing 722. In some embodiments, the range of movement may be constrained by engagement between the posts 705*a-b* and the compliant component 716.

In some embodiments, the compliant component 716 may be at least partially compressed when the probe 700 is assembled. The compression may be applied to the compliant component 716 by the housing 722. The compression of the compliant component 716 may cause the compliant component 716 to bias the transducer assembly 730 against the housing 722 at the distal end of the probe 700. The force applied by the compliant component 716 to the transducer assembly 730 may maintain alignment between the housing 722 and the transducer assembly 730.

A compliant coupling of the transducer assembly 730 to the housing 722 as described herein may reduce damage to the transducer assembly 730. For example, when a force is applied to the lens 736, the compliant component 716 may allow the transducer assembly 730 to move from the distal end towards the proximal end of the probe 700. In some embodiments, the boss 740 may prevent movement of the transducer assembly 730 beyond the boss 740. This may prevent excess movement of the transducer assembly 730 and may prevent the transducer assembly 730 from damaging the PCA 718 and/or other components of the probe 700. In some embodiments, the boss 740 may have an elastomeric cap 741 or coating. The elastomeric cap 741 may absorb at least some of an impact force when the transducer assembly 730 contacts the boss 740. In some embodiments, the sealant 731 may deform when a force is applied to the lens 736. In some embodiments, sealant 731 may maintain a seal between the housing 722 and the lens 736 along a periphery of the opening 725 even when a force is applied to the lens 736. The housing 722 may include a handle heat spreader 720 on an interior surface 721.

The handle heat spreader 720 may conduct heat from the transducer assembly 730, PCA 718, and/or other probe components and dissipate the heat through the housing 722. In some embodiments, the handle heat spreader 720 may be a thermally conductive coating applied to the interior surface 721 of the housing 722. In some embodiments, the handle heat spreader 720 may be a sheet of thermally conductive material shaped to conform to the interior surface 721 of the housing 722. In some embodiments, the conductive material may comprise copper.

Figure 8:
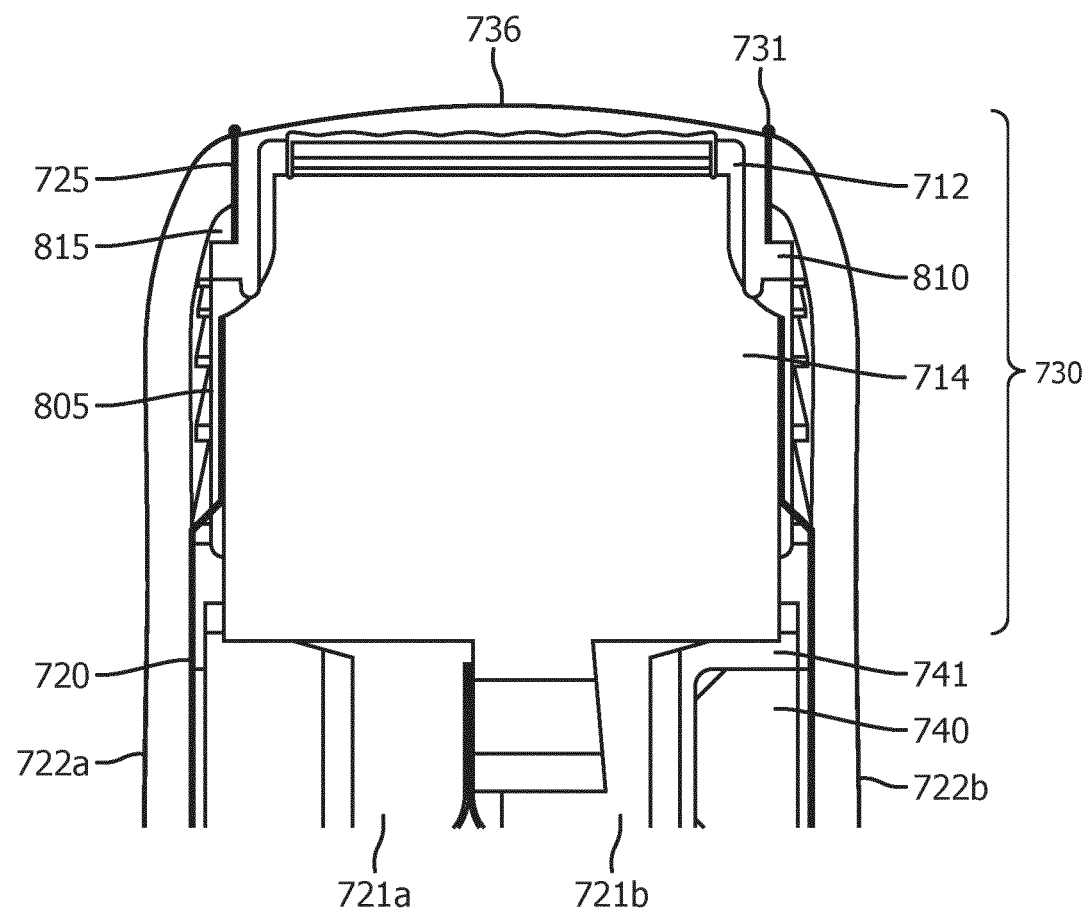
FIG. 8 is a schematic illustration of a partial cross-sectional side view of the distal end of the ultrasound probe shown in FIG. 7.

FIG. 8 is an enlarged side cross-sectional view of a portion of the ultrasound probe, specifically of the distal end of the ultrasound probe 700, shown in FIG. 7. At least a portion of the handle heat spreader 720 may be in thermal contact with one or more sides of the backing subassembly 714 of the transducer assembly 730. In some embodiments, a compressible block 805 may be coupled between the handle heat spreader 720 and an interior surface 721 of the housing 722. The compressible block 805 may be on an exterior-facing surface of the handle heat spreader 720 opposite the backing subassembly 714. The compressible block 805 may bias the handle heat spreader 720 into contact with the backing subassembly 714 when the probe 700 is assembled. The compressible block 805 may increase thermal contact between the backing subassembly 714 the heat spreader 720. In some embodiments, the compressible block 805 may be implemented with a polymer foam.

In some embodiments, a portion of the handle heat spreader 720 biased against the backing subassembly 714 may be coated with a laminate (not shown) that may reduce thermal resistance. Alternatively, the backing subassembly 714 may be coated with the laminate on a surface adjacent to the handle heat spreader 720. The laminate may improve heat transfer from the backing subassembly 714 to the handle heat spreader 720. An example of a possible laminate is Therm-a-Gap™ G974 available from Parker Chomerics. Other laminates that reduce thermal resistance may also be used.

In some embodiments, the transducer assembly 730 may be shaped to mate with the housing 722 of the ultrasound probe 700. For example, the backing subassembly 714 may be shaped to engage with an interior surface 721 of the housing 722. In some embodiments, the transducer assembly 730 may include features configured to engage with features of the housing 722. For example, in the embodiment shown in FIG. 8, the lens 736 includes a rim 810. The rim 810 may be configured to engage ledge 815 on an interior surface 721 of the housing 722. When the compliant component 716 is at least partially compressed, the compliant component 716 may apply a force on the transducer assembly 730, which may bias the rim 810 of the lens 736 against the ledge 815 of the housing 722. Features such as the rim 810 and ledge 815 may maintain alignment of the transducer assembly 730 with the housing 722. In some embodiments, the rim 810 may be included on the backing subassembly 714 instead of the lens 736. In some embodiments, the rim 810 may be replaced with ribs or tabs that extend from a periphery of the lens 736 or backing subassembly 714. The ribs or rim may be configured to engage with ribs or other features of the housing 722. In some embodiments, the ledge 815 may be a continuous ledge along the interior surface 7 21. In some embodiments, the ledge 815 is one of a plurality of ledges spaced along the interior surface 721.

Figure 9:
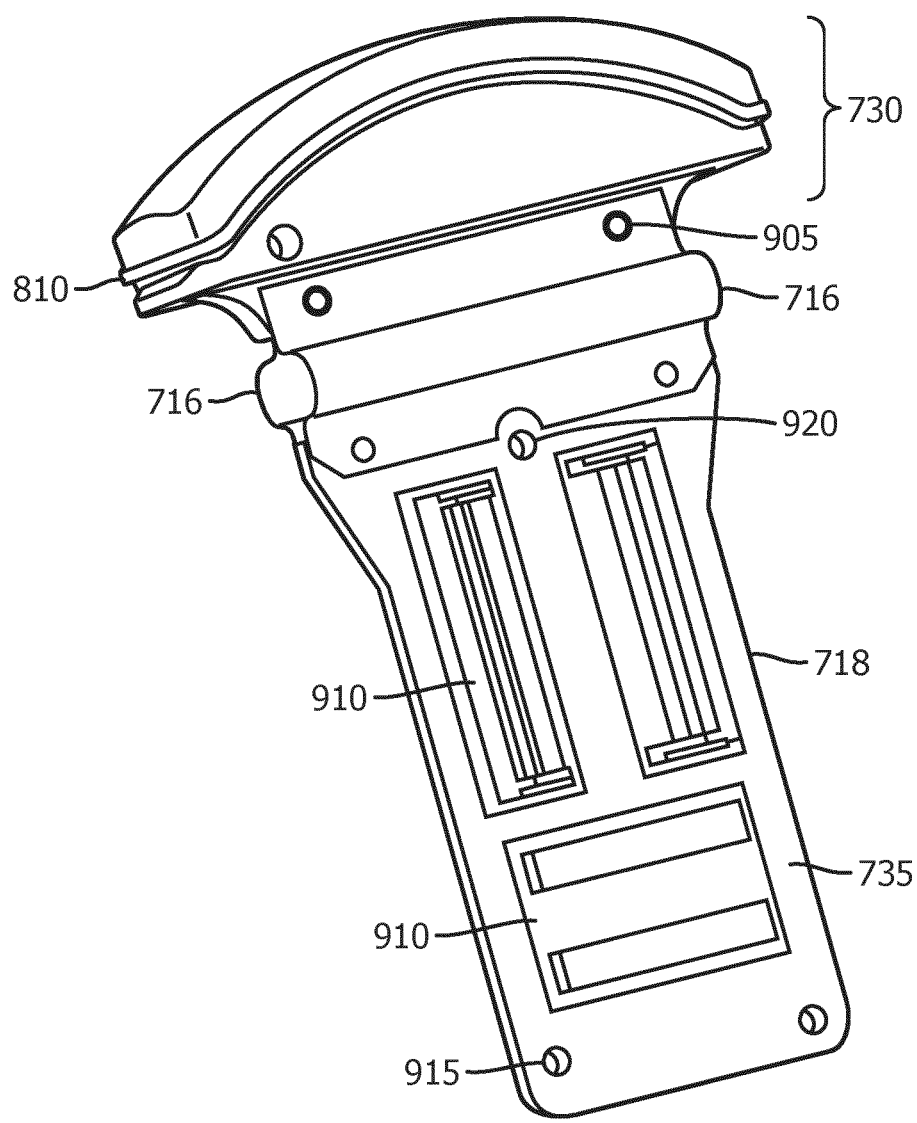
FIG. 9 is a schematic illustration of components of the ultrasound probe shown in FIG. 7.

FIG. 9 is a front view of the transducer assembly 730, compliant component 716, and PCA 718 of the ultrasound probe 700 shown in FIGS. 7-8. In some embodiments, as shown in FIG. 9, holes 905 may be included in the compliant component 716 and/or transducer assembly 730. The holes 905 may engage mechanical fasteners (e.g., screws) to couple the compliant component 716 to the transducer assembly 730. Similarly, in some embodiments, as shown in FIG. 9, holes 915 may be included in the PCA 718. In some embodiments, posts 715a and/or 715b may pass through the holes 915. In some embodiments, the holes 915 may engage mechanical fasteners to couple the PCA 718 to the housing 722 (not shown) of the probe 700. Hole 920 be included in the PCA 718. In some embodiments, post 705a and/or 705b may pass through hole 920. Although two holes 905, one hole 920, and two holes 915 are shown, more or fewer holes may be used in some embodiments. The cladding 735 may be patterned to include windows 910. The windows 910 may provide access to electrical connections of the PCA 718. The windows 910 may allow a flexible circuit (not shown) of the transducer assembly 730 to be coupled to circuitry on the PCA 718. Although three windows 910 are shown, more or fewer windows may be used in some embodiments.

In some embodiments, heat from the transducer assembly 730 may be conducted through the compliant component 716 to the distal end of the PCA 718. The heat may be conducted from the distal end to the proximal end of the PCA 718. In some embodiments, the heat may be conducted by the cladding 935 of the PCA 718. In some embodiments, at least a portion of the transducer assembly 730 (e.g., backing subassembly), the compliant component 716, at least a portion of the PCA 718 (e.g., cladding), the handle heat spreader 720, and/or at least a portion of the cable (e.g., metal braid) may be components of a thermal management system of the ultrasound probe 700.

Figure 10:
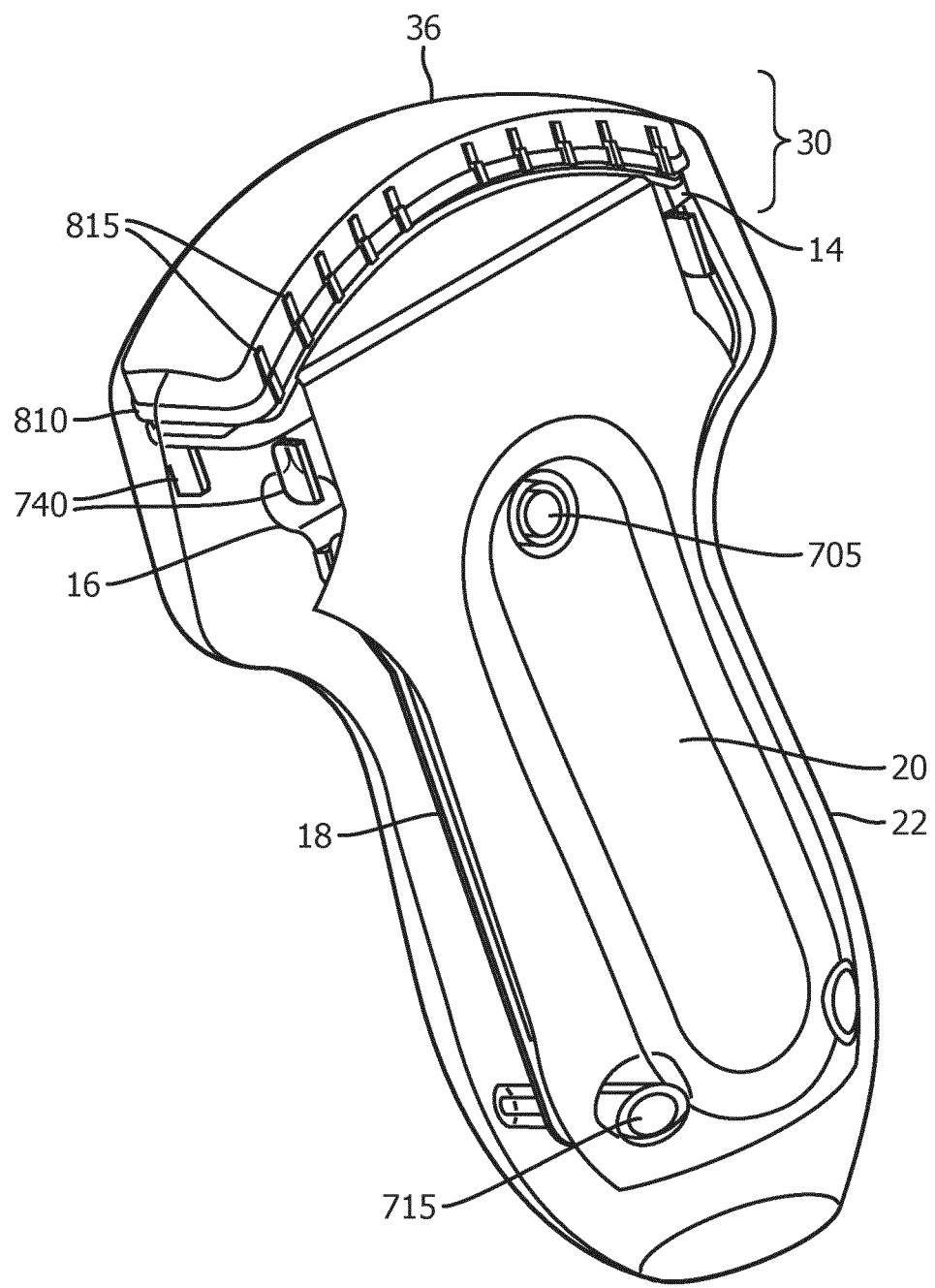
FIG. 10 is another schematic illustration of components of the ultrasound probe shown in FIG. 7.

FIG. 10 is an isometric view of the ultrasound probe 700 shown in FIG. 7. The housing 722 has been rendered translucent to illustrate an arrangement of at least some of the components within the housing 722 according to an embodiment of the disclosure. In some embodiments, the handle heat spreader 720 conforms to the interior surface (not visible in FIG. 10) of the housing 722. The handle heat spreader 720 may be coupled to the housing 722 by an adhesive in some embodiments. The adhesive may be thermally conductive. In some embodiments, the handle heat spreader 720 may be press-fit to the housing 722. In some embodiments, the handle heat spreader 720 may be a coating or film applied and/or deposited in the housing 722.

In the embodiment illustrated in FIG. 10, the rim 810 of the lens 736 is continuous and the ledge 815 of the housing 722 is implemented as a plurality of spaced ledges. The ledges 815 engage the rim 810. The ledges 815 may at least partially maintain alignment between the transducer assembly 730 and the housing 722.

In the embodiment illustrated in FIG. 10, boss 740 is implemented as a plurality of bosses. The bosses 740 project from the housing 722 between the proximal end of the backing subassembly 714 and the distal end of the compliant component 716. The movement of the transducer assembly 730 may be constrained between the ledges 815 and the bosses 740 in some embodiments.

Although ultrasound probes 10, 200, and 700 are described as separate embodiments of the disclosure, embodiments that include combinations of ultrasound probes 10, 200, and 700 may be implemented. For example ultrasound probe 200 may include a handle heat spreader in some embodiments. In another example, ultrasound probe 700 may include posts only on one side of the housing and couple the PCA to the posts with screws in some embodiments. Other combinations may be possible. In some embodiments, ultrasound probe 10, 200, or 700 may be a wireless probe. That is, a cable may not be coupled to the PCA, and the ultrasound probe may communicate wirelessly with an ultrasound imaging system. Heat generated by the transducer stack of the wireless probe may be conducted by the thermal management system to the probe housing, for example, by a handle heat spreader, and dissipated into the environment external to the ultrasound probe.

The thermally conductive compliant component has been described as an S-shaped spring and a C-shaped spring, however, other configurations may be used to implement the compliant component. For example, the compliant component may be implemented as a block of compressible foam embedded with a thermally conductive material placed between the transducer assembly and the PCA. In another example, the compliant component may be implemented as one or more pistons comprising a thermally conductive material. In a further example, one or more scissor mechanisms comprising a thermally conductive material may be used. These examples are provided as illustrations and are not meant to limit embodiments of the thermally conductive compliant component.

The thermal management system of the ultrasound probe may be a passive thermal management system in some embodiments. This may reduce cost, size, and weight requirements of the probe compared to an active thermal management system. The thermal management system may include a backing subassembly of a transducer array, a thermally conductive compliant component, cladding of a PCA, and a handle heat spreader located in the ultrasound probe housing in thermal contact with one another. The thermal management system may conduct heat from a transducer stack of the probe. The thermally conductive compliant component may reduce peak impact forces experienced by the transducer assembly and/or other ultrasound probe components compared to when a backing subassembly and internal probe frame are rigidly coupled to dissipate heat from the transducer stack. This may prevent or reduce damage to the lens, transducer stack, and/or other ultrasound probe components when the ultrasound probe is dropped. This may reduce repair and/or replacement costs.

Figure 11:
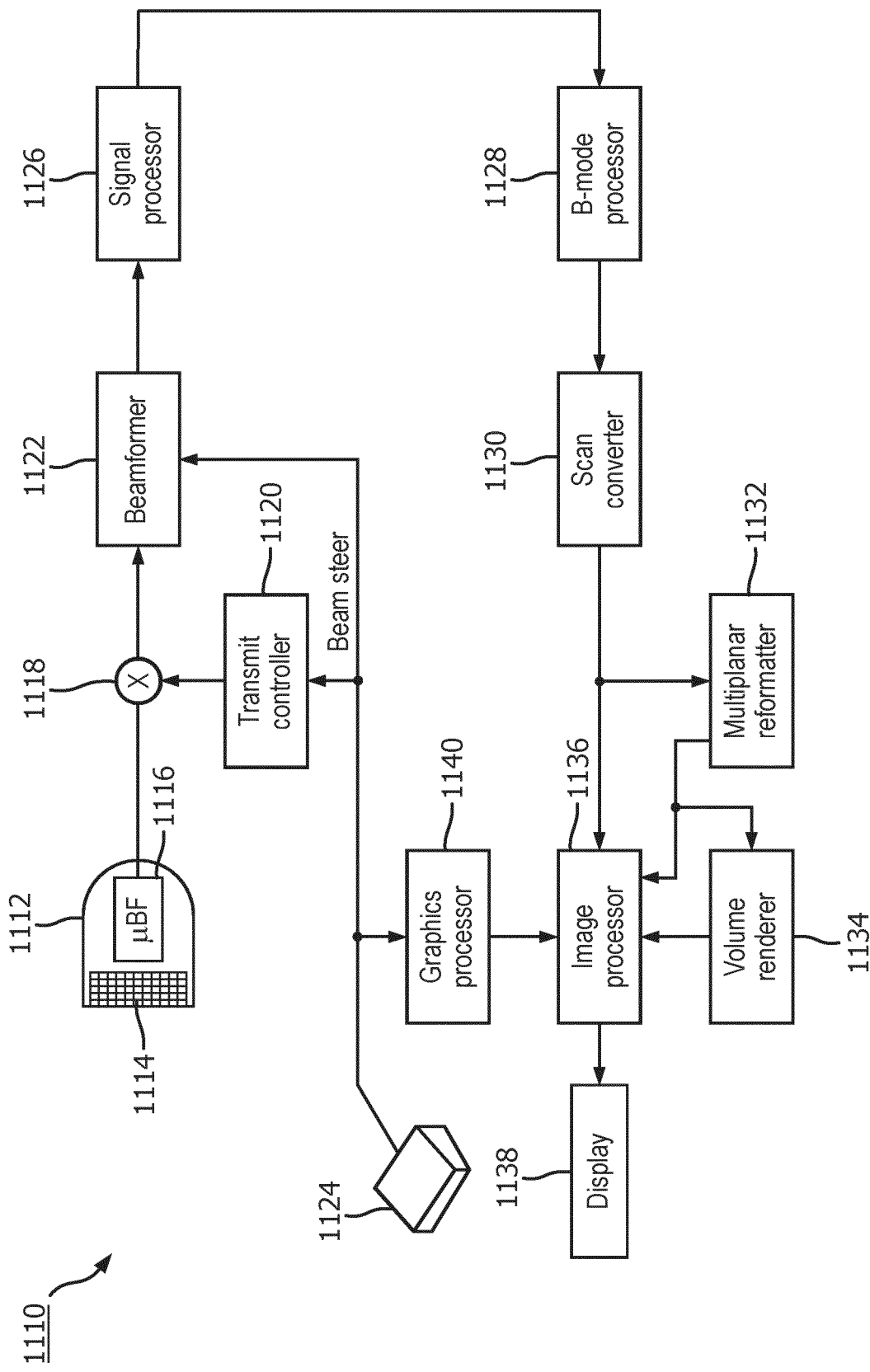
FIG. 11 is a block diagram of an ultrasound imaging system according to an embodiment of the disclosure.

Referring to FIG. 11, an ultrasound imaging system 1110 constructed in accordance with the principles of the present disclosure is shown in block diagram form. The ultrasound imaging system 1110 includes an ultrasound probe 1112, which may be implemented using ultrasound probe 10, 200, or 700 in some embodiments. In the ultrasonic diagnostic imaging system of FIG. 11, an ultrasound probe 1112 includes a transducer array 1114 for transmitting ultrasonic waves and receiving echo information. A variety of transducer arrays are well known in the art, e.g., linear arrays, convex arrays or phased arrays. The transducer array 1114, for example, can include a two dimensional array (as shown) of transducer elements capable of scanning in both elevation and azimuth dimensions for 2D and/or 3D imaging. The transducer array 1114 is coupled to a microbeamformer 1116 in the probe 1112 which controls transmission and reception of signals by the transducer elements in the array. In this example, the microbeamformer is coupled by the probe cable to a transmit/receive (T/R) switch 1118, which switches between transmission and reception and protects the main beamformer 1122 from high energy transmit signals. In some embodiments, the T/R switch 1118 and other elements in the system can be included in the transducer probe rather than in a separate ultrasound system base. The transmission of ultrasonic beams from the transducer array 1114 under control of the microbeamformer 1116 is directed by the transmit controller 1120 coupled to the T/R switch 1118 and the beamformer 1122, which receives input from the user's operation of the user interface or control panel 1124. One of the functions controlled by the transmit controller 1120 is the direction in which beams are steered. Beams may be steered straight ahead from (orthogonal to) the transducer array, or at different angles for a wider field of view. The partially beamformed signals produced by the microbeamformer 1116 are coupled to a main beamformer 1122 where partially beamformed signals from individual patches of transducer elements are combined into a fully beamformed signal.

The beamformed signals are coupled to a signal processor 1126. The signal processor 1126 can process the received echo signals in various ways, such as bandpass filtering, decimation, I and Q component separation, and harmonic signal separation. The signal processor 1126 may also perform additional signal enhancement such as speckle reduction, signal compounding, and noise elimination. The processed signals are coupled to a B mode processor 1128, which can employ amplitude detection for the imaging of structures in the body. The signals produced by the B mode processor are coupled to a scan converter 1130 and a multiplanar reformatter 1132. The scan converter 1130 arranges the echo signals in the spatial relationship from which they were received in a desired image format. For instance, the scan converter 1130 may arrange the echo signal into a two dimensional (2D) sector-shaped format, or a pyramidal three dimensional (3D) image. The multiplanar reformatter 1132 can convert echoes which are received from points in a common plane in a volumetric region of the body into an ultrasonic image of that plane, as described in U.S. Pat. No. 6,443,896 (Detmer). A volume renderer 1134 converts the echo signals of a 3D data set into a projected 3D image as viewed from a given reference point, e.g., as described in U.S. Pat. No. 6,530,885 (Entrekin et al.) The 2D or 3D images are coupled from the scan converter 1130, multiplanar reformatter 1132, and volume renderer 1134 to an image processor 1136 for further enhancement, buffering and temporary storage for display on an image display 1138. The graphics processor 1136 can generate graphic overlays for display with the ultrasound images. These graphic overlays can contain, e.g., standard identifying information such as patient name, date and time of the image, imaging parameters, and the like. For these purposes the graphics processor receives input from the user interface 1124, such as a typed patient name. The user interface can also be coupled to the multiplanar reformatter 1132 for selection and control of a display of multiple multiplanar reformatted (MPR) images.

Further examples of inventive subject matter are disclosed in the enumerated paragraphs below:

A1. A thermal management system, comprising:
 a backing subassembly of a transducer assembly;
 a cladding on an exterior surface of a printed circuit assembly (PCA), wherein the cladding is spaced from and coupled to the backing subassembly; and
 a compliant component disposed between the backing subassembly and the cladding and coupling the backing subassembly to the cladding, wherein the compliant component is configured to enable a distance between the cladding and the backing subassembly to vary.

A2. The thermal management system according to paragraph A1, wherein the cladding is soldered to the compliant component.

A3. The thermal management system according to paragraph A1, wherein the compliant component is clamped to the cladding.

A4. The thermal management system according to any of paragraphs A1-A3, further comprising a handle heat spreader in thermal contact with the backing subassembly.

A5. The thermal management system according to any of paragraphs A1-A4, further comprising a cable in thermal contact with the cladding.

Although the present system has been described with reference to an ultrasound imaging system, the present system may be extended to other ultrasound transducers. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is thermal dissipation and reduction of impact forces in ultrasound transducers and method of operation thereof is provided. Another advantage of the present systems and method is that conventional medical imaging systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound probe, comprising:
a transducer assembly at a distal end of the ultrasound probe, the transducer assembly comprising:
a lens,
a transducer stack coupled to the lens,
a backing subassembly coupled to a side of the transducer stack opposite the lens, and
a thermal laminate applied to the backing subassembly;
a printed circuit assembly (PCA) spaced from and coupled to the transducer assembly;
a housing enclosing the PCA and at least a portion of the transducer assembly, wherein the housing defines an opening at the distal end of the probe to expose at least a portion of the lens through the opening; and
a thermally conductive compliant component disposed between the transducer assembly and the PCA and coupling the transducer assembly to the PCA, wherein the thermally conductive compliant component is configured to bias the transducer assembly away from the PCA towards the opening in the housing, wherein the coupling of the transducer assembly to the PCA via the thermally conductive compliant component includes mechanical coupling and thermal coupling, and wherein the thermally conductive compliant component is in thermal contact with the thermal laminate of the transducer assembly,
wherein the thermally conductive compliant component comprises a spring having a first end connected to a distal portion of the PCA and a second end connected to a proximal portion of the backing subassembly,
and further wherein the at least one spring comprises an S-shaped or C-shaped strip of metal.

2. The ultrasound probe of claim 1, wherein the first end of the S-shaped strip of metal comprises a pair of flanges, each disposed on an opposite side of the distal portion of the PCA.

3. The ultrasound probe of claim 1, wherein the thermally conductive compliant component comprises a plurality of C-shaped springs each extending between the PCA and the backing subassembly.

4. The ultrasound probe of claim 1, wherein the housing at a periphery of the opening is coupled to a periphery of the lens by a sealant.

5. The ultrasound probe of claim 1, wherein the PCA includes a cladding on an exterior surface, wherein the cladding is coupled to the thermally conductive compliant component.

6. The ultrasound probe of claim 1, further comprising a heat spreader on an interior surface of the housing, wherein the heat spreader is thermally coupled to a side of the backing subassembly.

7. The ultrasound probe of claim 6, further comprising a compressible block between the housing and the heat spreader, wherein the compressible block is configured to bias the heat spreader against the side of the backing subassembly.

8. The ultrasound probe of claim 1, further comprising a cable coupled to a proximal end of the PCA, wherein the PCA is configured to conduct heat from the thermally conductive compliant component to the cable.

9. The ultrasound probe of claim 8, wherein the cable includes a metal braid coupled to the PCA.

10. The ultrasound probe of claim 1, wherein an interior surface of the housing includes ribs adjacent to the transducer assembly, and wherein the backing subassembly includes tabs configured to engage the ribs and align the lens with the opening in the housing.

11. The ultrasound probe of claim 10, wherein the interior surface of the housing includes posts adjacent to opposite sides of a distal end of the PCA, wherein the posts are configured to constrain the PCA and wherein the thermally conductive compliant component is compressed between the ribs and the posts of the housing.

12. The ultrasound probe of claim 1, wherein an interior surface of the housing includes a post adjacent to a proximal end of the PCA and the PCA is coupled to the housing by a screw that passes through the PCA and engages with the post.

13. The ultrasound probe of claim 1, wherein the thermal laminate, the thermally conductive compliant component, and at least a portion of the PCA are included in a thermal management system of the ultrasound probe.

14. An ultrasound imaging system comprising:
an ultrasound probe comprising:
a transducer assembly at a distal end of the probe, the transducer assembly comprising:
a lens
a transducer stack coupled to the lens
a backing subassembly coupled to a side of the transducer stack opposite the lens, and
a thermal laminate applied to the backing subassembly;
a printed circuit assembly (PCA) spaced from and coupled to the transducer assembly;
a housing enclosing the PCA and at least a portion of the transducer assembly, wherein the housing defines an opening at the distal end of the probe to expose at least a portion of the lens through the opening; and
a thermally conductive compliant component disposed between the transducer assembly and the PCA and coupling the transducer assembly to the PCA, wherein the thermally conductive compliant component is configured to bias the transducer assembly away from the PCA towards the opening in the housing, wherein the coupling of the transducer assembly to the PCA via the thermally conductive compliant component includes mechanical coupling and thermal coupling, and wherein the thermally conductive compliant component is in thermal contact with the thermal laminate of the transducer assembly,
wherein the thermally conductive compliant component comprises a spring having a first end connected to a distal portion of the PCA and a second end connected to a proximal portion of the backing subassembly, and further wherein the at least one spring comprises an S-shaped or C-shaped strip of metal;

an image processor configured to receive signals from the ultrasound probe and generate an image; and a display configured to display the image received from the image processor.

15. The ultrasound imaging system of claim 14, wherein the housing at a periphery of the opening is coupled to a periphery of the lens by a sealant.

16. The ultrasound imaging system of claim 14, wherein the PCA includes a cladding on an exterior surface, wherein the cladding is coupled to the thermally conductive compliant component.

17. The ultrasound imaging system of claim 14, further comprising a heat spreader on an interior surface of the housing, wherein the heat spreader is thermally coupled to a side of the backing subassembly.

* * * * *